US006488998B1

(12) United States Patent
Crook

(10) Patent No.: US 6,488,998 B1
(45) Date of Patent: *Dec. 3, 2002

(54) PIPE WRAP FOR PREVENTING MICROBIOLOGICALLY INFLUENCED CORROSION IN BURIED CONDUITS

(75) Inventor: John A. Crook, Birmingham, AL (US)

(73) Assignee: Fulton Enterprises, Inc., Birmingham, AL (US)

( * ) Notice: Subject to any disclaimer, the term of this patent is extended or adjusted under 35 U.S.C. 154(b) by 136 days.

This patent is subject to a terminal disclaimer.

(21) Appl. No.: 09/630,195

(22) Filed: Aug. 1, 2000

Related U.S. Application Data

(63) Continuation-in-part of application No. 09/223,603, filed on Dec. 30, 1998, now Pat. No. 6,183,825, which is a continuation-in-part of application No. 08/669,111, filed on Jun. 24, 1996, now Pat. No. 6,224,957.

(51) Int. Cl.[7] ........................... A01N 25/34; B32B 27/30
(52) U.S. Cl. .................... 428/36.91; 428/461; 428/515; 428/516; 428/523; 424/411; 424/412; 138/141; 138/146
(58) Field of Search ................................. 428/515, 516, 428/523, 36.91, 461; 424/411, 412; 138/141, 146, DIG. 6

(56) References Cited

U.S. PATENT DOCUMENTS

| | | | |
|---|---|---|---|
| 2,937,665 A | 5/1960 | Kennedy | |
| 3,024,153 A | 3/1962 | Kennedy | |
| 3,033,724 A | 5/1962 | Stokes | |
| 3,157,204 A | 11/1964 | Phillips | |
| 3,223,571 A | 12/1965 | Straughan | |
| 3,231,443 A | 1/1966 | McNulty | |
| 3,425,954 A | 2/1969 | Ruzevick et al. | |
| 3,469,002 A | 9/1969 | Moyer et al. | |
| 3,565,747 A | 2/1971 | Vincent et al. | |
| 3,687,765 A | 8/1972 | MacLean et al. | |
| 3,692,619 A | 9/1972 | Wedekind et al. | |
| 3,877,490 A | 4/1975 | Tsubouchi et al. | |
| 4,035,546 A | 7/1977 | Ruppert, Jr. | |
| 4,051,066 A | 9/1977 | Miksic et al. | |
| 4,211,595 A | 7/1980 | Samour | |
| 4,213,486 A | 7/1980 | Samour et al. | |
| 4,254,165 A | 3/1981 | Phelps et al. | |
| 4,290,912 A | 9/1981 | Boerwinkle et al. | |
| 4,321,297 A | 3/1982 | Adelman | |
| 4,331,480 A | 5/1982 | Gutman et al. | |
| 4,374,174 A | 2/1983 | Stricklin et al. | |
| 4,472,231 A | 9/1984 | Jenkins | |
| 4,499,136 A | 2/1985 | Nakamura et al. | |
| 4,533,435 A | 8/1985 | Intili | |
| 4,557,966 A | 12/1985 | Weil | |
| 4,617,328 A | 10/1986 | Liu | |
| 4,631,302 A | 12/1986 | Supcoe et al. | |
| 4,670,499 A | 6/1987 | Bonnke et al. | |
| 4,752,629 A | 6/1988 | Proudlock et al. | |
| 4,789,692 A | 12/1988 | Rei et al. | |
| 4,824,705 A | 4/1989 | Persson et al. | |
| 4,853,297 A | 8/1989 | Takahashi et al. | |
| 4,973,448 A | 11/1990 | Carlson et al. | |
| 4,983,449 A | 1/1991 | Nee | |
| 4,988,236 A | 1/1991 | Ramsey et al. | |
| 5,006,185 A | 4/1991 | Anthony et al. | |
| 5,104,390 A | 4/1992 | Yum et al. | |
| 5,139,700 A | 8/1992 | Miksic et al. | |
| 5,209,869 A | 5/1993 | Miksic et al. | |
| 5,320,778 A | 6/1994 | Miksic et al. | |
| 5,417,676 A | 5/1995 | Watanabe et al. | |
| 5,465,527 A | 11/1995 | Able | |
| 5,489,281 A * | 2/1996 | Watanabe et al. | ............. 422/28 |
| 5,525,426 A | 6/1996 | Kulzick et al. | |
| 6,183,825 B1 * | 2/2001 | Crook | ........................ 138/141 |

FOREIGN PATENT DOCUMENTS

| | | |
|---|---|---|
| FR | 2400-663 | 8/1977 |
| SU | 974-027 A | 3/1979 |

OTHER PUBLICATIONS

"Synergistic Protection Against Microbiologically Influenced Corrosion Using a 100% Solids Polyurethane Incorporated with Anti–Microbial Agents" Author—Dr. Shiwei Guan Published—Between Aug. 1997 and Nov. 1997.

* cited by examiner

*Primary Examiner*—D. Lawrence Tarazano
(74) *Attorney, Agent, or Firm*—Robert M. Jackson; Robert J. Veal; Burr & Forman LLP

(57) ABSTRACT

An improved anti-corrosive material used to protect buried conduits from corrosion. The anti-corrosive material is comprised of a conduit contacting layer of polyolefin having the anti-corrosive agents impregnated therein. The preferred embodiment of the material is a multi-layered co-extruded, calendered, or laminated polyolefin. The material has an outer layer, or environment contacting layer, preferably comprised of a low density polyethylene having characteristically strong tensile strength and elongation properties to provide conventional protection from soil, water, air, or other potentially damaging elements. The material has a center layer preferably comprised of a high density polyethylene having superior tensile strength to provide a high density barrier between the outer layer and an inner layer. The inner layer, or conduit contacting layer, is preferably comprised of a low density polyethylene impregnated with one or more antimicrobial additives. The antimicrobial additives are incorporated into and dispersed throughout the conduit contacting layer for killing corrosion-inducing bacteria on the surface of the conduit. The antimicrobial additives are able to migrate through the low density polymer matrix but the rate of migration of the biocide is considerably slowed through the high density polymer. Thus, the antimicrobial agents are substantially prevented from escaping into the surrounding environment, but rather, are trapped within a "protection zone" immediately adjacent the conduit surface to provide extended protection against corrosion.

7 Claims, No Drawings

PIPE WRAP FOR PREVENTING MICROBIOLOGICALLY INFLUENCED CORROSION IN BURIED CONDUITS

RELATED MATERIALS

The present application is a continuation-in-part application of pending U.S. patent application Ser. No. 09/223,603, filed Dec. 30, 1998 now U.S. Pat. No 6,183,825, which is incorporated herein by reference. Application Ser. No. 09/223,603 is a continuation-in-part application of patent application Ser. No. 08/669,111, filed Jun. 24, 1996 now U.S. Pat. No. 6,224,957, which is also incorporated herein by reference.

FIELD OF THE INVENTION

The present invention relates to an improved anti-corrosive material. Particularly, the present invention relates to a protective material for preventing microbiologically influenced corrosion in buried conduits. More particularly, the present invention relates to a multi-layered material used to encase buried conduits to prevent corrosion.

BACKGROUND OF THE INVENTION

Buried conduits are ubiquitously used for carrying various materials, such as water, natural gas, oil, and sewage. A major problem with buried conduits comprised of metal or concrete with metal reinforcements is corrosion. The severity and rate of corrosion is dependent on the type of material comprising the conduit and the environment in which the conduit is buried. Insuring the longevity of buried conduits is an important part of the infrastructure in the United States and the world. Significant costs are involved in design, development, manufacture, and installation of water, gas, and sewage systems. Failure of these systems from conduit corrosion represents appreciable costs.

The control of corrosion of metals has been a quest of producers and consumers for the entire history of ferrous materials. Corrosion is typically understood to be the result of oxidation and/or galvanic processes. Historically, corrosion prevention has primarily addressed the reduction of oxygen component or control of galvanic action to prevent the occurrence of corrosion. Some typical corrosion prevention processes are painting or coating the metal to prevent oxygen from reaching the surface, volatile corrosive inhibitors that remove the available oxygen, and/or cathodic protection. Even after utilizing all the currently available mechanisms for the prevention of corrosion there are instances where unexplained corrosion occurs in buried metal pipes and conduits.

In the 1930's, the mechanisms of Microbiologically Influenced Corrosion ("MIC") were proposed by Von Wolzen Kuhr to explain corrosion initiated or accelerated by microorganisms. Since that time, studies have shown the Von Wolzen Kuhr theory to be valid, and it has been established that a consortium of microorganisms contribute to many metal corrosion failures. These microorganisms, alone or more typically in combination, include as follows:

Sulphate-reducing bacteria including Desulfovibrio, Desulfobacter, and Desulformaculum. Sulphate-reducing bacteria are anaerobic and are the primary cause of Microbiologically Influenced Corrosion. Sulphate-reducing bacteria are associated with the reduction of sulphate under anaerobic conditions and an associated production of hydrogen sulfide, which creates an alkaline environment that can accelerate corrosion.

Iron-oxidizing bacteria including Gallionella, Sphaerotilus, Leptothrix, Clonothrix, and Crenothrix. Iron-oxiding bacteria are associated with the oxidization of various forms of iron and, in some cases, an associated production of ferric chloride and an acidic environment that can accelerate corrosion.

Sulfur-oxidizing bacteria including Thiobacillus, Thiodendron, Beggiatoa, and Sulfolobus. Sulfur-oxiding bacteria are aerobic bacteria that form sulphuric acid, which is corrosive to many metals, from the oxidation of sulphur or sulphur-bearing compounds.

Slime-forming bacteria including Pseudomonas, Escherichia, Flavobacterium, Aerobacter and Bacillus.

Susan Watkins Borenstein, *Microbiologically Influence Corrosion Handbook* ch. 2 (1994).

Hereto, no one has effectively addressed the elimination of the microbiologically influenced corrosion occurring in buried metal pipes and conduits. For example, ductile iron pipe (DIP) typically exhibits a low risk to severe corrosion compared to other metals; however, a rapid increase in the corrosion rate can be initiated by oxygenated water, tidal action, or specific soil types such as soils containing sulfides. Because of the high costs associated with removal and replacement of corroded conduits, the industry has expended substantial resources attempting to solve this problem.

Initially, conduits were covered with paint coatings, wraps, or other materials to separate the conduit surfaces from the environment. However, specialized coatings are either susceptible to deterioration by sulfate-reducing bacteria or are sophisticated to the point that they are no longer cost effective. Later, barrier films of polyethylene were used to protect DIP conduits. By insulating the exposed surfaces from soil, electrical currents, and oxygenated water, corrosion is usually prevented. However, due to improper installation, tears and punctures to the barrier film occurring during the installation and backfill process, free flow of water from tidal action, or soil or water becoming entrapped between the film and the conduit surface, actual corrosion still occurs in many cases. The industry has attempted to solve these problems by using more durable barrier films to encase the conduit surfaces, such as high density cross-laminated polyethylenes (HDCLPE). The superior impact strength, tear resistance, and tensile strength of HDCLPE has reduced some of the problems associated with the installation and backfill process; however, HDCLPE does not adequately address or control the problem of microbiologically influenced corrosion. Since there has not been an adequate alternative, present industry standards typically use either an 8 mil low density polyethylene (LDPE) film or a 4 mil HDCLPE film, a mil being equal to one thousandth of an inch (0.0254 millimeter), to wrap around the conduits for protection against corrosion.

Polyethylenes, as well as other plastic films, limit the free flow of water against the conduit surfaces, thereby reducing available oxygen. Any moisture that becomes trapped between the film and the conduit surface will eventually become deaerated. A problem arises where deaerated water levels are attained in the presence of the previously identified sulfate reducing bacteria. Many anaerobic bacteria, such as *Desulfovibrio desulfuricans,* thrive in certain fresh water, brackish water, sea water, sulfate soils, or warm soil conditions. These bacteria act as a catalyst to initiate or augment the rate of corrosion in an environment that is normally adverse to corrosion, and as previously noted are a primary cause of microbiologically influenced corrosion. Additionally, other types of bacteria are believed to play a part in corrosion propagation and it appears that bacteria are also responsible for degradation of the polyethylene film. A possible solution to this problem is to treat the materials used to encase the conduit with bactericides. However, most bactericides are topical and water soluble, thereby offering only initial protection that loses their effectiveness when used in buried systems exposed to wet conditions. Since conduits are buried for decades, this would not provide adequate long-term protection.

Another possible solution is to use certain volatile corrosion inhibitors (VCIs) which can be introduced either in contact or near the metal surface to eliminate or reduce the presence of corrosion. An example of a commonly used VCI is illustrated in U.S. Pat. No. 3,425,954. These VCIs can be used to prevent conditions from developing inside the film barrier which are favorable to corrosion. VCIs work at a micron level to passivate the surface of metal with a passive film, thus reducing the chemical reactivity of its surface. VCIs are normally used in kraft papers for short term protection of metal parts, as illustrated in U.S. Pat. No. 4,557,966; however, paper is not suitable to be buried. VCIs could be added to the polyethylene film, but the effectiveness will be shortened since the vapor tends to escape from the film, thus preventing extended protection. VCIs also lose their effectiveness when used in buried systems. An additional possible solution is the practice of isolating the system to prevent corrosion due to galvanic action; however this technique is ineffective against bacterial corrosion. However, currently available methods for controlling conduit corrosion do not address microbiologically influenced corrosion, or their application is technically complex and very expensive, or they are not suitable for buried conduits From the foregoing it may be seen that hereto, no one has adequately addressed the elimination of the microbiologically influenced corrosion element for the long-term protection of buried conduits. A need exists for an improved anti-corrosive material for protecting conduits buried in conditions favorable to microbiologically influenced corrosion.

SUMMARY OF THE PRESENT INVENTION

It is the object of the present invention to provide an improved anti-corrosive material which is superior to those presently used to protect buried conduits.

It is an additional object of the present invention to provide an improved anti-corrosive material that provides long term protection of buried conduit by preventing microbiologically influenced corrosion.

It is another object of the present invention to provide a material that contains an antimicrobial additive to prevent bacterial-induced or enhanced corrosion.

It is a further object of the present invention to provide a material that contains volatile corrosion inhibitors to prevent corrosion.

It is another object of the present invention to provide an anti-corrosive material comprising a conduit-contacting layer having an antimicrobial additive impregnated therein, incorporated into and dispersed throughout the conduit-contacting layer such that the antimicrobial additive can migrate within the conduit-contacting layer to contact the conduit surface and thereby prevent microbiologically influenced or enhanced corrosion therein.

It is another object of the present invention to provide a multi-layered, anti-corrosive material having a barrier layer adjacent the conduit-contacting layer that prevents the antimicrobial additive from penetrating the barrier layer and entering the surrounding environment.

It is still a further object of the present invention to provide a material which is co-extruded, calendered, or laminated into a multi-layered material comprising a conduit contacting layer having antimicrobial additives impregnated therein, incorporated into and dispersed throughout the conduit contacting layer such that the anti-corrosive agents can migrate within the conduit contacting layer to contact the conduit surface and prevent corrosion.

It is yet a further object of the present invention to provide a material which is co-extruded, calendered, or laminated into a multi-layered material further comprising a barrier layer adjacent the conduit contacting layer which prevents the anti-corrosive agents from penetrating the barrier layer and escaping into the surrounding environment.

These and other objects of the present invention are accomplished through the use of an improved anti-corrosive material used to protect buried conduits from corrosion. Incorporated into the improved anti-corrosive material are antimicrobial additives that effectively eliminate bacteria associated with microbiologically influenced corrosion. The additives can be blended with polyethylene raw materials in a manner that disperses the material throughout the product and be insoluble in aqueous conditions. Since the additive is designed as a contact agent, a requirement of manufacture is that proper dispersion and percent content be effected to generate the proper barrier against microbial growth. A test program was implemented to develop the proper polyethylene film manufacturing techniques that would yield proper protective characteristics. This product is a new cost effective anti-corrosive material used to protect buried conduits comprising ductile iron, steel, or concrete reinforced with steel by reducing or eliminating previously unexplained failures of buried conduits caused or accelerated by microbiologically influenced corrosion.

The anti-corrosive material is comprised of a conduit contacting layer of polyolefin having the anti-corrosive agents impregnated therein. The anti-corrosive agents, or antimicrobial additives, are incorporated into and dispersed throughout the conduit contacting layer such that the anti-corrosive agents can migrate within the conduit contacting layer to contact the conduit surface and prevent corrosion.

Another embodiment of the anti-corrosive material is a multi-layered co-extruded, calendered, or laminated polyolefin. The material has an outer layer, or environment contacting layer, preferably comprised of a low density polyethylene having characteristically strong tensile strength and elongation properties to provide conventional protection from soil, water, air, or other potentially damaging elements. The material has a center layer preferably comprised of a high density polyethylene having superior tensile strength to provide a high density barrier between the outer layer and an inner layer. The inner layer, or conduit contacting layer, is preferably comprised of a low density polyethylene impregnated with an antimicrobial additive such as a biocide or a volatile corrosion inhibitor (VCI), or both. The antimicrobial additive is incorporated into and dispersed throughout the conduit contacting layer for killing corrosion-inducing bacteria on the surface of the conduit. The antimicrobial agents are able to migrate through the low density polymer matrix but the rate of migration of the antimicrobial additive is considerably slowed through the high density polymer and the VCI is essentially unable to penetrate it. Thus, the antimicrobial agents are substantially prevented from escaping into the surrounding environment, but rather, are trapped within a "protection zone" immediately adjacent the conduit surface to provide extended protection against corrosion.

The present invention is not limited to simply overcoming the deficiencies of the prior art but introduces enhanced technical advantages in corrosion protection that were not previously available for the long term protection of buried conduits while continuing to meet established industry standards.

These and other objects and advantages of the invention will become apparent from the following detailed description of the preferred embodiment of the invention.

DETAILED DESCRIPTION OF THE PREFERRED EMBODIMENT

An anti-corrosive material embodying features of the invention is comprised of a multi-layered co-extruded, calendered, or laminated polyolefin. The preferred embodiment of the present invention is comprised of 3 layers with a total thickness of 8 mils, to conform to the industry standard film thickness. It is to be understood that the following description is for purposes of illustration only and that the thickness of the film as a whole or the individual layers, or the method of producing the layers, can be altered from that described herein without departing from the spirit of the invention. Additionally, the polyolefin of choice is polyethylene but others such as polypropylene, ethylene/vinyl acetate copolymers, vinyl acetate/vinyl chloride copolymers, or polyvinyl chloride could be substituted.

The outermost layer, or environment contacting layer, provides conventional protection from soil, water, air, or other potentially damaging elements. The outermost layer typically comprises 4 mils of low density polyethylene (LDPE), preferably linear low density polyethylene (LLDPE), having characteristically strong tensile strength and elongation properties. This deters punctures and tears during handling and the backfill process. LDPE has a density range between approximately 0.910 to 0.925. The purpose of the outer layer is to provide conventional protection; therefore, biaxially oriented LDPE, medium density polyethylene (MDPE), or high density polyethylene (HDPE) could be substituted. MDPE has a density range between approximately 0.926 to 0.940. The center layer typically comprises 2 mils of HDPE, having a density greater than approximately 0.94. This layer possesses superior tensile strength and provides a high density barrier acting to prevent any anti-corrosive agents impregnated within the innermost, or conduit contacting layer from migrating through the center layer and escaping into the environment.

The innermost, or conduit contacting layer preferably comprises a 2 mil LDPE, although a linear or biaxially oriented LDPE or MDPE could be substituted. This layer is impregnated with an antimicrobial additive such as a biocide or a volatile corrosion inhibitor (VCI), or both. The antimicrobial additives are incorporated into and dispersed throughout the conduit contacting layer for killing corrosion-inducing bacteria on the surface of the conduit. The antimicrobial additives must be able to withstand the temperature required to melt and process the polyolefin. In the preferred embodiment, the antimicrobial additive is 2,4,4'-trichloro-2'-hydroxy diphenyl ether (triclosan) (e.g., ULTRA FRESH®-NM-100, Thomson Research Associates, Ontario, Canada), which has been found to be effective at low concentrations against a wide range of bacteria, including those associated with microbiologically influence corrosion.

Although 2,4,4'-trichloro-2'-hydroxy diphenyl ether is the antimicrobial additive of the preferred embodiment, it is understood that another antimicrobial additive can be chosen. Other antimicrobials that either kill a broad spectrum of organisms or a specific organism associated with microbiologically influenced corrosion include bromonitropropanediol (e.g., ULTRA FRESH®-SAB, Thomson Research Associates, Ontario, Canada); organotin (e.g., ULTRA FRESH®-DM-50, Thomson Research Associates, Ontario, Canada), diiodomethyl-p-tolyl sulfone (e.g., ULTRA FRESH®-95, Thomson Research Associates, Ontario, Canada), halogenated aromatic nitrites, imazilil sulfate salts, 3,5,3',4'tetrachlorosalicylanilide, dichlorophene, hexachlorophene, dioxin, ethyl benzoate, methyl benzoate, and methyl p-hydroxy-benzoate. Some of these antimicrobial additives are presently used in kraft. See e.g., U.S. Pat. Nos. 3,469,002; 4,401,712; and 4,533,435.

The antimicrobial additive is blended into molten LDPE resin which will be used in forming the innermost layer. The LDPE and antimicrobial additive are typically mixed at about 400 degrees Fahrenheit; however, the temperature should not exceed about 425 degrees Fahrenheit because the antimicrobial additive can begin to irreversibly denature or evaporate. The molten material is then ready to be extruded to form the innermost layer. The final concentration of biocide is approximately 0.01% to 10.0% by weight, with a preferred concentration of 0.5% to 2.0% although this can vary depending on the type of antimicrobial additive used and the environment to be used in. The antimicrobial additive is partially bound to the polyolefin matrix such that some antimicrobial additive is retained within the polymer matrix to prevent bacterial growth, while unbound antimicrobial additive will slowly migrate through the polymer matrix toward the conduit surface to prevent bacterial growth. The migration of antimicrobial additive is considerably slowed by the high density center layer; thus the antimicrobial additive is kept within a "protection zone" comprising the inner layer and conduit surface. The slow migration of the antimicrobial additive within the polymer matrix towards the conduit provides low levels of antimicrobial additive to the conduit surface for an extended period of time.

Although a VCI is not used in the preferred embodiment, if a VCI is used as an antimicrobial agent VCI is preferably comprised of nitrates or nitrites, which are proven effective corrosion inhibitors for one or more of the organisms associated with microbiologically influenced corrosion. Other VCIs may also be used, including triazoles, carbonates, phosphates, molybdates, and aliphatic or aromatic amines. See e.g. U.S. Pat. Nos. 4,973,448 and 5,139,700. VCIs operate by passivating the metal, or reducing the chemical reactivity of its surface; thus stopping or reducing corrosion rates that occur under the film. Typically, VCI is blended with molten polyethylene resin, at about 400 degrees Fahrenheit, which will be used in forming the innermost layer; however, again the temperature should not exceed about 425 degrees Fahrenheit because the VCI will evaporate. The molten material is then ready to be extruded to form the innermost layer. The final concentration of VCI is typically between approximately 1% to 5% by weight of the innermost layer, preferably 2% to 3%, although this can vary depending on the type of VCI used and the environment to be used in.

The VCI is not bound to the polyolefin matrix and LDPE has a measurable rate of moisture and vapor transmission, thus the VCI slowly migrates toward the conduit since it is too large to pass through the center layer, resulting in long-term protection of the conduit surface. Some gas transmission rates of LDPE and HDPE are:

|  | Oxygen¹ | Water Vapor* |
| --- | --- | --- |
| LDPE | 500–450 | 1–2 |
| LDPE (Biaxially Oriented) | 350–400 | 0.3–0.5 |
| LDPE (Linear) | 300–400 | 0.5–1.0 |
| HDPE | 150–200 | 0.3–0.5 |

¹cc mil/100 sq. in./24 hrs. at 72 degrees Fahrenheit
*gm mil/100 sq. in./24 hrs. at 100 degrees Fahrenheit, 90% Relative Humidity After the materials for each layer have been prepared, the material is co-extruded, calendered, or laminated into a two or three layered product. The process of co-extruding, calendering, and laminating multi-layered film is well known in the art and will not be described herein. It is especially important to note that the innermost layer of the anti-corrosive material may be impregnated with one or more antimicrobial additives depending on the intended use. The antimicrobial additives are incorporated into and dispersed throughout the conduit contacting layer for killing corrosion-inducing bacteria on the surface of the conduit.

Additionally, the anti-corrosive material could be comprised from only one layer of polyolefin having the anti-corrosive agents impregnated therein, or comprised of a material having a plurality of layers with any number of layers having the anti-corrosive agents impregnated therein. The spirit of the present invention is providing a material which is comprising a conduit contacting layer having antimicrobial additives impregnated therein so that the antimicrobial additives are incorporated into and dispersed throughout the conduit contacting layer such that the anti-corrosive agents can migrate within the conduit contacting layer to contact the conduit surface and prevent corrosion. This material can be adapted for use with not only underground conduits but also storage tanks, building foundations, etc.

The VCI has an additional benefit of limiting bacterial growth responsible for other problems, such as degradation of rubber gaskets or the polyethylene film. Another benefit of using the multi-layered material is seen where some municipalities require color coating for underground conduits indicating the class of materials contained within the conduit. With the multi-layered product, only the exterior layer must be colored, thus reducing the costs from color additives that would otherwise have been needed for the entire film (including all component layers).

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. An apparatus for carrying fluids, comprising:

a conduit comprising a material selected from the group consisting of metal, and concrete with metal reinforcements;

a polyolefin film comprising an anti-corrosive film layer in abutment with a surface of said conduit, said anti-corrosive film layer having an antimicrobial additive incorporated into and dispersed throughout said anti-corrosive film layer for killing corrosion-inducing bacteria on the surface of said conduit, said antimicrobial additive being selected from the group consisting of bromonitropropanediol, 2,4,4'-trichloro-2'-hydroxy diphenyl ether, and diiodomethyl-p-tolyl sulfone.

2. The apparatus described in claim 1 wherein said polyolefin film further comprises a barrier film layer having a permeability resistant to migration of said antimicrobial additive therethrough adjacent said anti-corrosive layer to maintain said antimicrobial additive in an anti-corrosion zone comprising said anti-corrosive layer and the surface of said conduit.

3. The apparatus described in claim 2 wherein said polyolefin film further comprises an outer protective film layer adjacent said barrier film layer.

4. The apparatus described in claim 1, 2 or 3 wherein said antimicrobial additive is between 0.01% to 10.0% by weight of said anti-corrosive layer.

5. The apparatus described in claim 1, 2 or 3 wherein said anti-corrosive layer comprises a material selected from the group consisting of low density, medium density, and high density polyethylenes.

6. The apparatus described in claim 1, 2 or 3 wherein said barrier layer comprises a material selected from the group consisting of low density, medium density, and high density polyethylenes.

7. The apparatus described in claim 3 wherein said outer layer comprises a material selected from the group consisting of low density, medium density, and high density polyethylenes.

\* \* \* \* \*